United States Patent
Baldauf

(10) Patent No.: US 7,670,662 B2
(45) Date of Patent: Mar. 2, 2010

(54) LAMINATE MATERIAL ELEMENT FOR A HOOK AND LOOP CLOSURE, PARTICULARLY A DIAPER CLOSURE

(75) Inventor: Georg Baldauf, Laer (DE)

(73) Assignee: Nordenia Deutschland Gronau GmbH, Gronau (DE)

(*) Notice: Subject to any disclaimer, the term of this patent is extended or adjusted under 35 U.S.C. 154(b) by 0 days.

(21) Appl. No.: 11/130,957

(22) Filed: May 17, 2005

(65) Prior Publication Data

US 2006/0182927 A1 Aug. 17, 2006

(30) Foreign Application Priority Data

Feb. 12, 2005 (EP) .................................. 05003001

(51) Int. Cl.
- B32B 3/00 (2006.01)
- B32B 3/06 (2006.01)
- B32B 33/00 (2006.01)
- B32B 27/00 (2006.01)

(52) U.S. Cl. ................ 428/99; 428/88; 428/100; 428/193; 428/194; 428/197; 428/198

(58) Field of Classification Search ................ 428/88, 428/99, 192, 193, 194, 100, 195.1, 196, 197, 428/198

See application file for complete search history.

(56) References Cited

U.S. PATENT DOCUMENTS

| | | | | |
|---|---|---|---|---|
| 4,931,343 A * | 6/1990 | Becker et al. | | 428/95 |
| 5,407,439 A * | 4/1995 | Goulait | | 604/391 |
| 5,569,233 A * | 10/1996 | Goulait | | 604/391 |
| 5,614,281 A * | 3/1997 | Jackson et al. | | 428/100 |
| 5,660,918 A * | 8/1997 | Dutta | | 428/196 |
| 5,736,214 A * | 4/1998 | Billarant | | 428/92 |
| 5,763,041 A * | 6/1998 | Leak et al. | | 428/100 |
| 5,876,532 A * | 3/1999 | Billarant | | 156/66 |
| 5,891,547 A * | 4/1999 | Lawless | | 428/92 |
| 6,589,638 B1 * | 7/2003 | McCormack et al. | | 428/198 |
| 6,705,132 B1 * | 3/2004 | Hajek | | 66/194 |
| 6,910,353 B2 * | 6/2005 | Sasser et al. | | 66/191 |
| 6,916,969 B1 * | 7/2005 | Helmfridsson et al. | | 604/378 |
| 7,083,691 B2 * | 8/2006 | Hamulski et al. | | 156/73.1 |
| 7,325,421 B2 * | 2/2008 | Sasser et al. | | 66/195 |
| 7,501,361 B2 * | 3/2009 | Baldauf | | 442/329 |
| 7,527,848 B2 * | 5/2009 | Baldauf | | 428/99 |
| 2002/0187696 A1 * | 12/2002 | Veiga et al. | | 442/76 |
| 2004/0058121 A1 * | 3/2004 | Schriefer et al. | | 428/99 |

(Continued)

FOREIGN PATENT DOCUMENTS

EP 0 777 006 B1 3/2002

*Primary Examiner*—Cheryl Juska
(74) *Attorney, Agent, or Firm*—Collard & Roe, P.C.

(57) ABSTRACT

A laminate material element (1) for a hook and loop closure, particularly a diaper closure, has a carrier film (2) and a textile material (3) laminated onto the carrier film (2), which has a surface structure that is suitable for forming a connection with the hooks of a hook and loop closure. The carrier film (2) and the textile material (3) are bonded together over their entire surface in an edge region that extends along the edges of the laminate material element and has the shape of a frame. A bond between the carrier film (2) and the textile material (3) that does not cover the entire surface is provided in the region within this frame.

9 Claims, 5 Drawing Sheets

U.S. PATENT DOCUMENTS

| | | | |
|---|---|---|---|
| 2004/0099019 A1* | 5/2004 | Sasser et al. | 66/195 |
| 2004/0099020 A1* | 5/2004 | Sasser et al. | 66/203 |
| 2004/0158957 A1* | 8/2004 | Horn et al. | 24/442 |
| 2005/0208260 A1* | 9/2005 | Baldauf | 428/95 |
| 2006/0080810 A1* | 4/2006 | Horn et al. | 24/445 |
| 2006/0180272 A1* | 8/2006 | Baldauf | 156/290 |
| 2007/0178273 A1* | 8/2007 | Provost et al. | 428/89 |
| 2008/0068393 A1* | 3/2008 | Yamazoe | 345/563 |
| 2008/0312680 A1* | 12/2008 | Blach et al. | 606/199 |

* cited by examiner

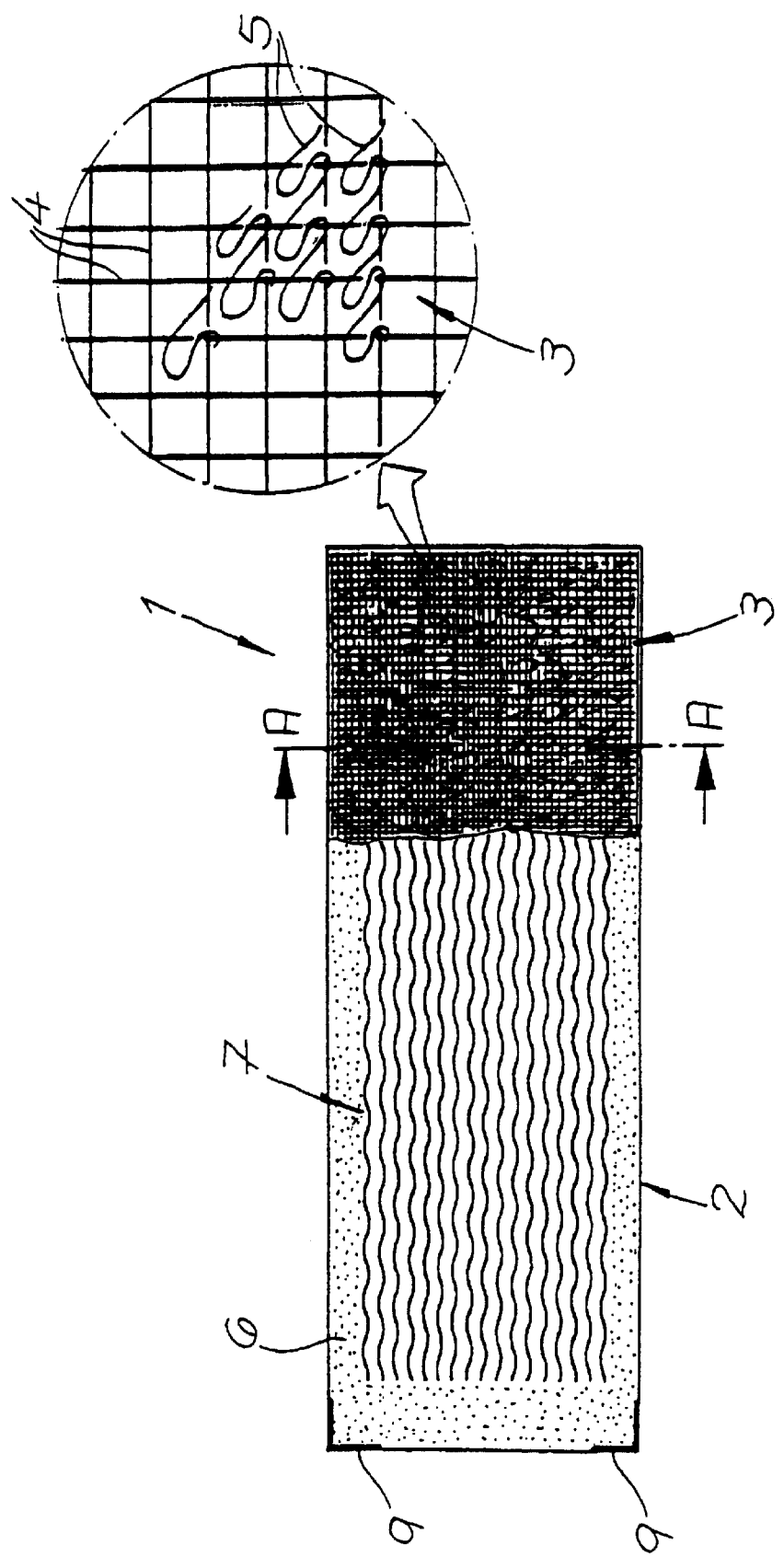

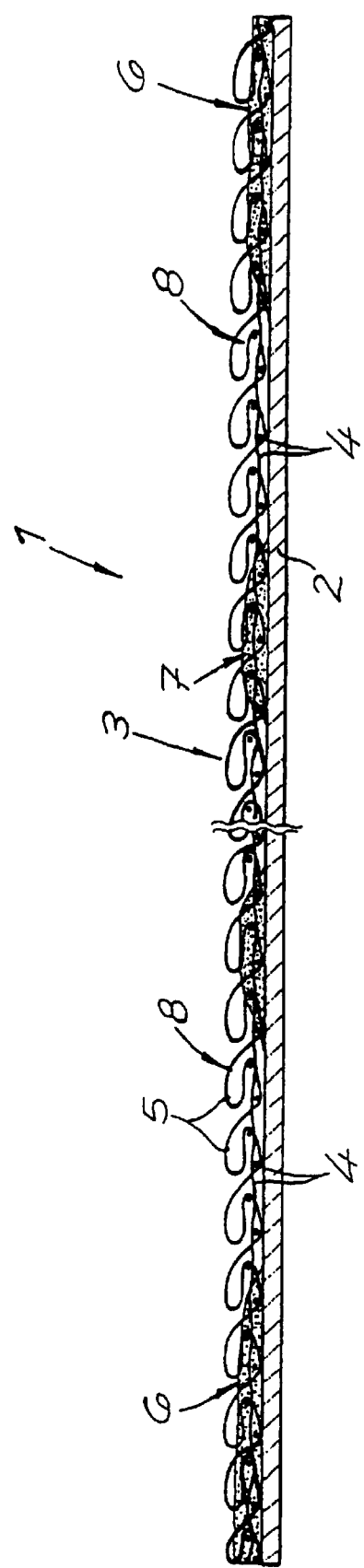

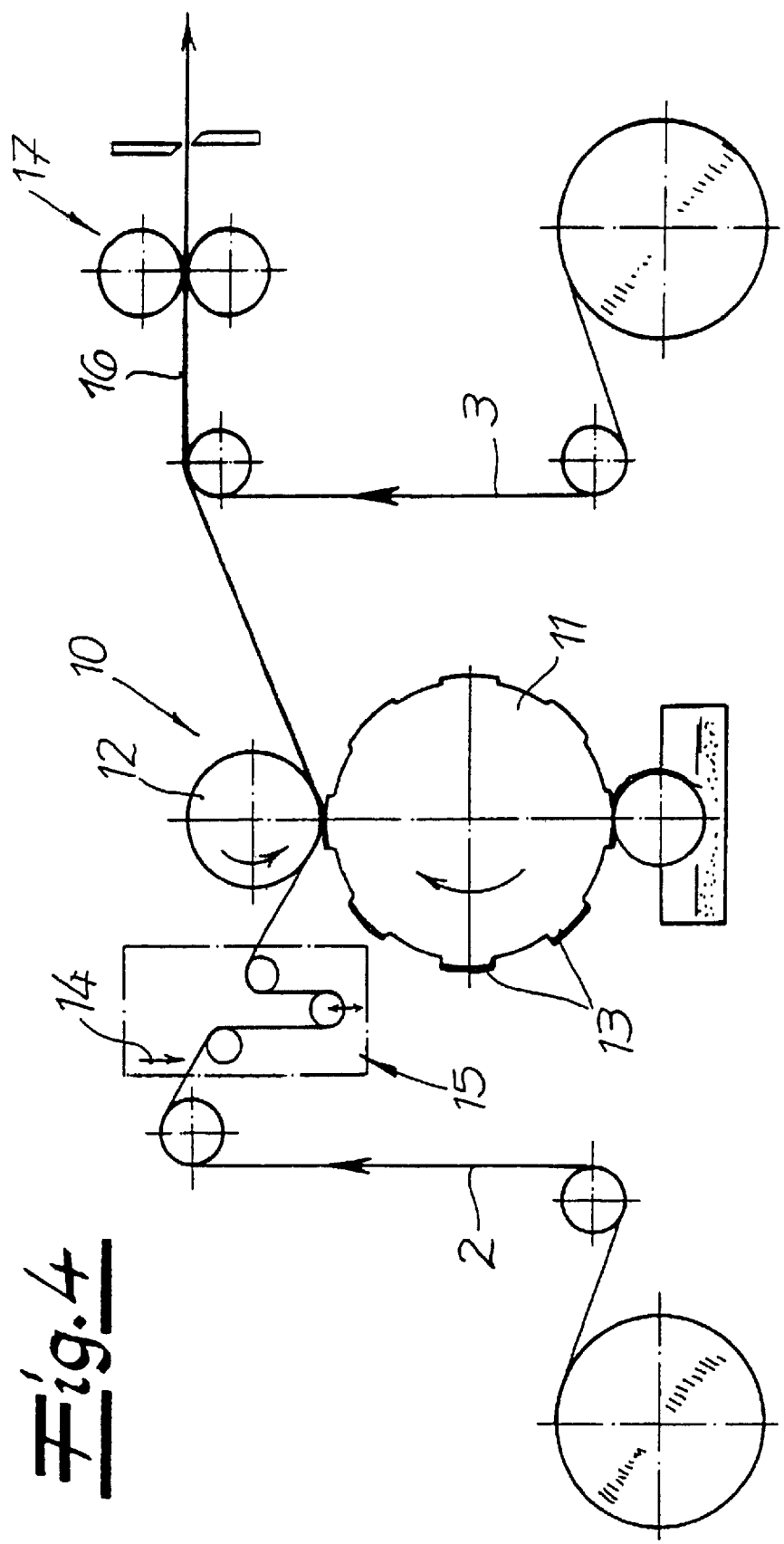

LAMINATE MATERIAL ELEMENT FOR A HOOK AND LOOP CLOSURE, PARTICULARLY A DIAPER CLOSURE

CROSS REFERENCE TO RELATED APPLICATIONS

Applicant claims priority under 35 U.S.C. §119 of European Application No. EP 05 003 001.4 filed Feb. 12, 2005.

Parties to a Joint Research Agreement

Nordenia Deutschland Gronau GmbH,
Jöbkesweg 11,
48599 Gronau, Germany, which is a German corporation, and
Procter & Gamble Service GmbH,
Sulzbacher Strasse 40,
65828 Schwalbach am Taunus, Germany, which is a German corporation, are parties to a Joint Research Agreement;

BACKGROUND OF THE INVENTION

1. Field of the Invention

The present invention relates to a laminate material element for a hook and loop closure, particularly a diaper closure, having a carrier film and a textile material laminated onto the carrier film, which has a surface structure that is suitable for forming a connection with the hooks of a hook and loop closure.

2. The Prior Art

The laminate material element forms the female part of a hook and loop closure. When used on diapers, the laminate material element is applied to the front waistband region of the diaper. A closure tape, which is attached at the side of the diaper and has hooks at its free end makes a hook and loop closure complete. Hook and loop closures can be opened and closed multiple times, without any deterioration of the functionality of the closure. In contrast to adhesive closures, hook and loop closures are not sensitive to contact with skin creams or powder.

Various demands are made on a laminate material element for a hook and loop closure on a disposable product, e.g. baby diapers. The textile material is supposed to have as low a weight per unit area as possible, so that it can be produced inexpensively. It is supposed to be translucent, so that the surface of the carrier film, which is generally imprinted, particularly also with trademarks imprinted on the film for further processing of the laminate material, remains visible. Furthermore, despite its low weight per unit area, the textile material must guarantee sufficient engagement with the hooks of the related closure tape. A sufficient number of freely movable loops and fibers is required, and their function is not allowed to be impaired by gluing the carrier film and the textile material together. In order to guarantee functionally reliable gluing of the textile material to the carrier film, a sufficiently thick film of adhesive must be applied. If the textile material and the carrier film are pressed against one another in a laminating unit, by means of a pair of rollers, the fibers of the textile material sink into the adhesive film and are surrounded by the adhesive film. After the adhesive film has cured, it is true that the yarns of the textile are securely anchored on the carrier film. However, large amounts of adhesive carry with them the risk that the loops and fibers that are needed for the function of the hook and loop closure are also glued in, and thereby lose their functionality. This becomes evident in an insufficient hook and loop effect.

A laminate material for hook and loop closures, having the characteristics described initially, is known from EP 0 777 006 B1. The textile material consists of an interlaid scrim of warp and weft threads, and loops connected with the interlaid scrim using knitting technology. The textile material is glued to the carrier film. The loops are sized to be so large that they rest on the smaller loops formed by the base interlaid scrim. The purpose of sizing the loops in this way is so that they do not come into contact with adhesive and thereby maintain their functionality. The problem explained above, that of assuring both a good hook and loop effect and a high laminate strength between the carrier film and the textile material, when using an open textile material, is not yet solved to the full extent, however. In particular, the bond between the carrier film and the textile material still requires improvement.

SUMMARY OF THE INVENTION

The present invention has as an object the configuring of the bond between the carrier film and the textile material of a laminate material element for a hook and loop closure in such a manner that an improved hook and loop result occurs, at high laminate strength, as compared with the state of the prior art.

This object is achieved, according to the present invention, in that the carrier film and the textile material are bonded together over their entire surface in an edge region that extends along the edges of the laminate material element and has the shape of a frame. Also, a bond between the carrier film and the textile material that does not cover the entire surface is provided in the region within this frame. By means of the bond over the entire surface, which extends in the shape of a frame along the edges of the laminate material element, the textile material is prevented from fraying. It is also prevented from being torn off from the carrier film when the hook and loop closure is activated, at the end of the laminate material element, where the greatest forces are applied when the hook and loop closure is opened, on the one hand, and the open ends of the textile material are present, on the other hand. Preferably, the edge region that is bonded over the entire surface has a width of 5 mm to 30 mm. The region within the frame preferably has a length between 20 mm and 100 mm, and a width between 50 mm and 500 mm.

A permanent bond between the carrier film and the textile material can be achieved by means of gluing. In this connection, the adhesive is applied over the entire surface, between the carrier film and the textile material, in the edge region of a laminate material element, and forms a frame of adhesive. The adhesive in the region enclosed by the adhesive frame is arranged in a pattern consisting of adhesive areas and regions that are free of adhesive, whereby the adhesive-covered area amounts to 20% to 80% with reference to the area surrounded by the adhesive frame. In the region of the adhesive-covered areas, a large amount of adhesive can be selected, thereby ensuring a secure, non-positive lock connection between the textile material and the carrier film. Thus, an extensive saturation of the textile material at the adhesive-covered surfaces can also be accepted. According to the present invention, the carrier film and the textile material lie loosely on top of one another in part of the laminated surface. These regions free of adhesive remain fully retained for the connection with the hook and loop hooks. The hook and loop hooks can hook into the textile material well there, since they can immerse themselves deep into the textile material. In addition to the superficial loops and fibers, the yarns that form the basic interlaid scrim of the textile material are also available for anchoring the hook and loop hooks, in the regions free of adhesive. The laminate material thereby gains a hook and loop effect that is significantly greater than when the textile material and the carrier film are glued together over their entire area.

In one embodiment according to the present invention, it comprises dividing the available connecting surface of the laminate up into adhesive areas that are formed by a frame and a pattern of adhesive, and producing a secure and durable bond between the carrier film and the textile material, and providing regions that are free of adhesive, in which a good hook and loop effect between the textile material and the hook and loop hooks is guaranteed.

In another embodiment according to the present invention, it can be implemented with a plurality of adhesive patterns within the adhesive frame at the edge of the laminate material element. Therefore, the present invention comprises gluing of the carrier film to the textile material in a dot pattern. Furthermore, there is the possibility that the adhesive forms a pattern of parallel or intersecting stripes, whereby the stripes can be configured as straight lines or as wave-shaped lines.

In a preferred embodiment of the present invention, the adhesive forms a pattern having a cell-shaped structure. Cell structures with open cells, free of adhesive, within the adhesive frame prove to be particularly effective. The textile material, which has a weight per unit area of between 5 g/m$^2$ and 50 g/m$^2$, for practical purposes, consists of a warp-knitted material. According to a preferred embodiment of the invention, which material has a basic interlaid scrim or filament yarns and loops connected with the basic interlaid scrim by means of knitting technology. This material is translucent and very air-permeable. This embodiment according to the present invention allows the processing of textile materials having a lower weight per unit area, to produce components of functional diaper closures. The textile material can be made of mono-filament and/or multi-filament yarns, particularly of polypropylene, polyester, polyamide, or other plastics that can be processed using textile technology.

According to a preferred embodiment, the carrier film also has a weight per unit area of between 5 g/m$^2$ and 50 g/m$^2$. Mono-films as well as well as multi-layer co-extruded or laminated films can be used. For example, films made of polyethylene, polypropylene, polyester, polyamide, as well as mixtures and co-polymerizates on the basis of these polymers are suitable. Preferably, carrier films are used whose surface can be imprinted using perfecting printing. Imprinted and/or embossed carrier films can be used.

By using an elastic film that is stretched during lamination, it is possible to achieve arcing of the textile material, and this can result in a further improvement in the hook and loop effect.

Fundamentally, all the adhesives used in the field of laminated films are suitable for gluing the textile material and the carrier film together. Hot-melt glues on the basis of PAO, EVA, SBS, SIS, reactive polyurethane adhesives, acrylate adhesives, as well as radiation-curing adhesives, are preferred.

Another object of the present invention is to provide a method for producing the laminate material elements described. Preferred embodiments of the method according to the invention are also described.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

FIG. 1 shows a top view of a laminate material element and its layers;

FIG. 2 shows a section through the laminate material element according to FIG. 1, along the line A-A;

FIG. 4 shows a method for the production of the laminate material; and

DETAILED DESCRIPTION OF PREFERRED EMBODIMENTS

Figure 3A:
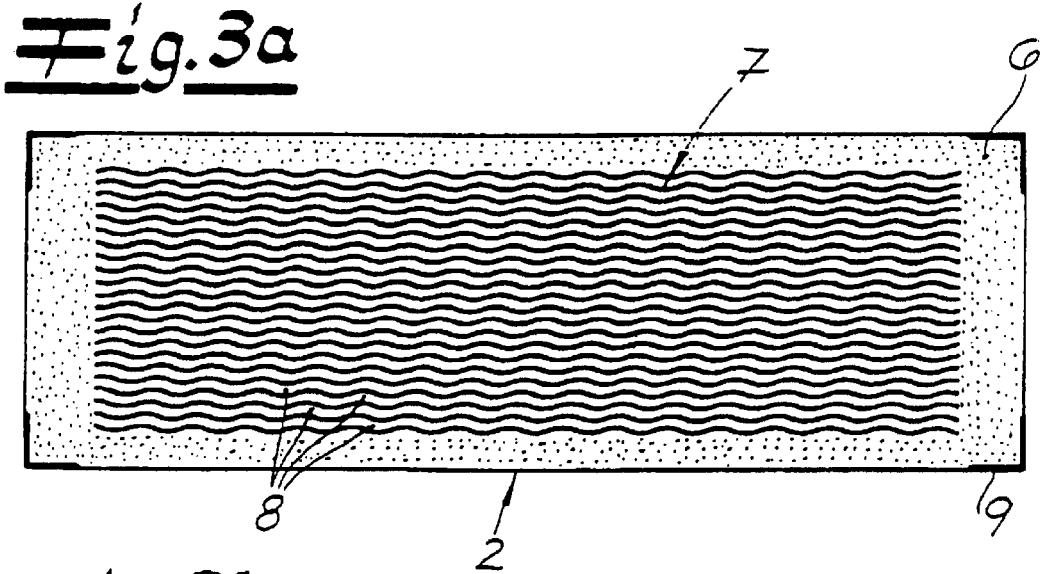
FIGS. 3a to 3d show adhesive patterns that form a connection layer between the carrier film and the textile material of the laminate material element shown in FIGS. 1 and 2.
Figure 3B:
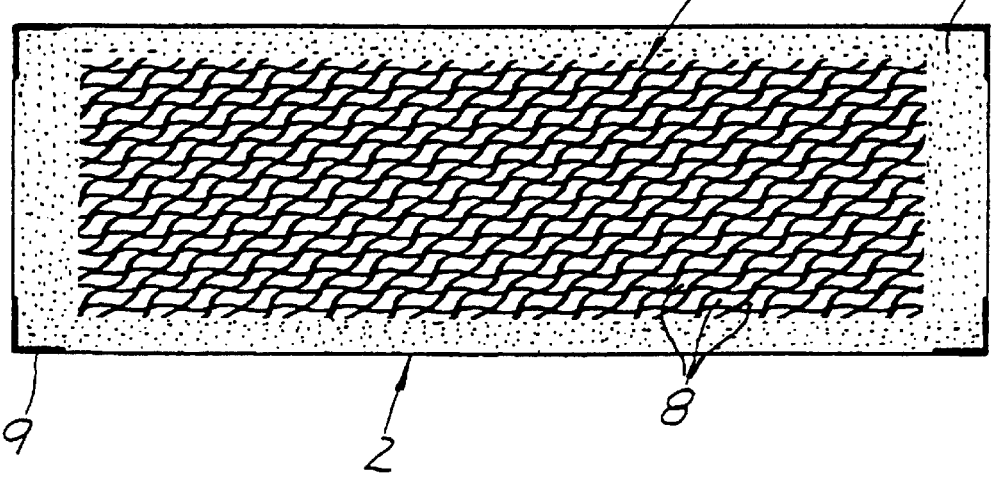

Turning now in detail to the drawings, the laminate material element 1 shown schematically in FIGS. 1 and 2 can be used as a female part of a hook and loop closure. The laminate material is particularly intended for hook and loop closures on disposable products, e.g. baby diapers. It includes a carrier film 2 and a textile material 3 laminated onto the carrier film, which has a surface structure that is suitable for forming a connection with hook and loop hooks. The material shown in FIGS. 1 and 2 is warp-knitted fabric having a basic interlaid scrim of filament yarns 4, as well as loops 5 connected with the basic interlaid scrim by means of knitting technology. The loops 5 are disposed on the surface and are suitable for being connected with hook and loop hooks of a closure tape, not shown.

The carrier film 2 and the textile material 3 are not connected with one another over their entire area. A full-area connection along the edge of the laminate material element 1, having a width between 5 mm and 30 mm, forms an adhesive frame 6, and has an internal adhesive pattern 7 with regions 8 that are free of adhesive. The proportion of the adhesive-covered area within the region surrounded by the adhesive frame 6 amounts to 20% to 80%, with reference to the area enclosed by the adhesive frame 6. At the adhesive areas, the textile material is firmly anchored to the carrier film 2, by means of applying adhesive. It is evident from FIG. 2 that the filament yarns 4 of the textile material 3 have sunk into the adhesive, for example a hot-melt glue, and are surrounded by it. In this connection, it can be accepted that the loops 5 are partially also glued in, in the region of the adhesive areas, and have only little effect in the region of the adhesive areas.

In the regions 8 that are free of adhesive, the carrier film 2 and the textile material 3 lie loosely on top of one another. Hook and loop hooks can be pushed deeply into the textile material 3 in the regions 8 of the laminate material that are free of adhesive. Thus, not only does hooking onto the superficial free loops 5 take place, but also, the filament yarns 4 of the basic interlaid scrim are available for anchoring the hook and loop hooks.

Thus, the hook and loop hooks can partly engage behind the filament yarns 4 of the textile material 3. The regions 8 of the laminate material that are free of adhesive are characterized by a great hook and loop effect, and impart good usage properties to the laminate material. By means of the adhesive frame 6 at the edge of the laminate material element 1, fraying of the edge of the textile layer, or even tearing of the textile layer from the carrier film 2, can be prevented even if the hook and loop closure is activated multiple times.

Figure 3C:
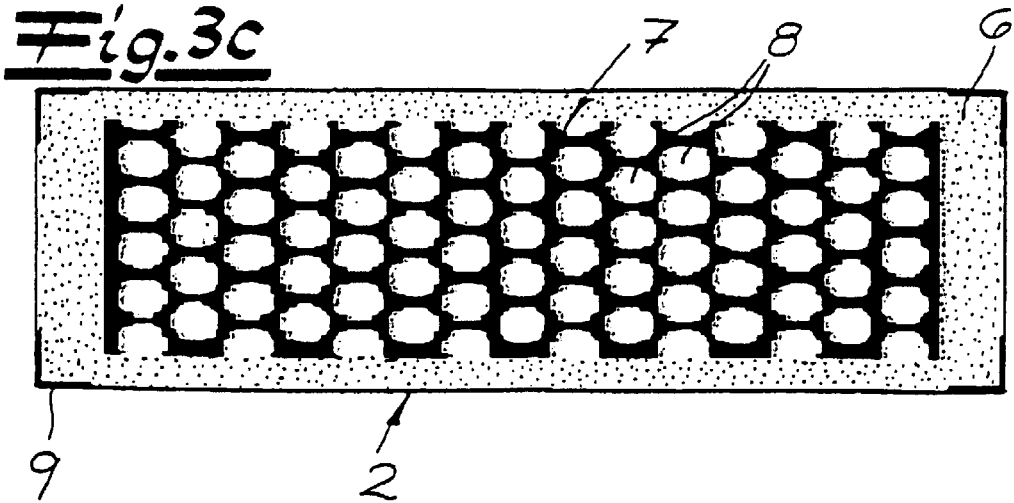
Figure 3D:
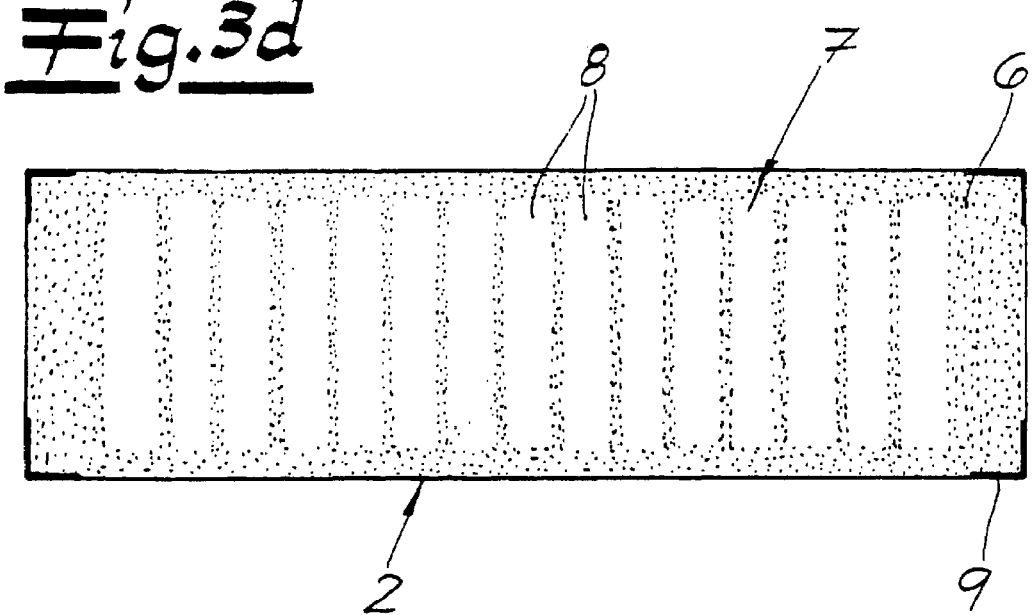
Figure 5:
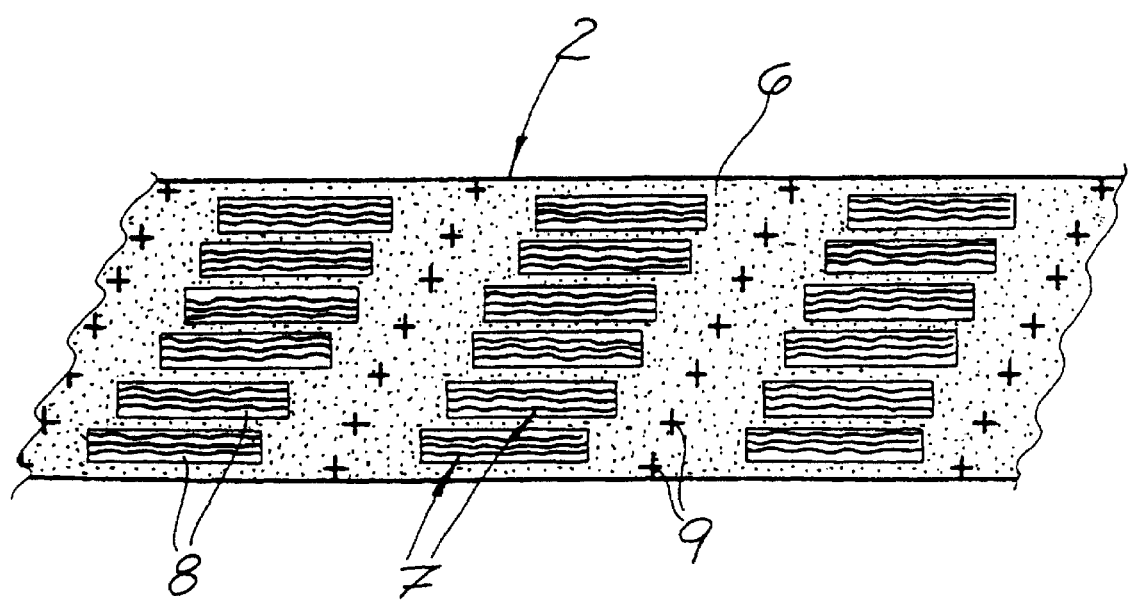
FIG. 5 shows a detail of a film web having the adhesive applied to it, before it is connected with the laminate material.

FIGS. 3a to 3d show various adhesive patterns 7 within the adhesive frame 6. In the embodiment of FIG. 3a, the adhesive forms a pattern of parallel stripes that run in a wave shape, within the adhesive frame 6. In another embodiment of FIG. 3b, the adhesive forms a pattern of intersecting stripes within the adhesive frame 6. FIG. 3c shows a further embodiment with a pattern having a cell-shaped structure within the adhesive frame 6, whereby the cell-shaped structure has closed cells with regions 8 that are free of adhesive. FIG. 3d shows a still further embodiment with a structure that comprises straight lines oriented parallel to the short sides of the rectangular laminate material element, within the adhesive frame 6. In all of these exemplary embodiments, the adhesive areas within the adhesive frames should amount to not less than 20% and at most 80% of the total surface area.

The textile material 3 preferably has a weight per unit area of between 5 and 50 g/m². It is permeable for air and is translucent. Therefore the carrier film 2 can be imprinted with a decorative pattern and/or register marks 9 for marking the adhesive frame 6. Films of polyolefins, polyester, polyamide, mixtures or co-polymerizates of these polymers can be used as carrier films 2. They preferably also have a weight per unit area of between 5 g/m² and 50 g/m².

To glue the carrier film 2 together with the textile material 3, hot-melt glues on the basis of PAO, EVA, SBS, SIS, reactive polyurethane adhesives, acrylate adhesives, as well as radiation-curing adhesives can be used, for example. The amounts of glue are coordinated with the adhesive area in such a manner that a firm bond between the carrier film 2 and the textile material 3 is guaranteed. Therefore the amounts of adhesive applied can be determined variably, as a function of the intended use.

A method for the production of the laminate material elements 1 is schematically shown in FIG. 4. Adhesive is applied to a carrier film 2 in a pattern that is composed of adhesive areas and regions 8 that are free of adhesive. The adhesive can be applied to the carrier film 2 by means of nozzle application methods, by means of spraying technology, or by means of similar methods.

In the case of the preferred embodiment of the method shown in the exemplary embodiments, the adhesive is applied to the carrier film according to the rotary printing method. In this case, the carrier film 2 passes through a printing roller arrangement 10 comprising an engraved cylinder 11 and a counter-cylinder 12 that presses the carrier film 2 against the engraved cylinder 11. Also, the surface of the engraved cylinder 11 is provided with an engraving 13 that corresponds to the adhesive pattern.

In the embodiment shown in FIG. 4, an adhesive is applied to the surface of the engraved cylinder 11, and transferred to the carrier film at the raised surfaces of the engraving 13. In order to position the adhesive frames 6 relative to register marks 9, which are already printed on the film web in the selected exemplary embodiment, the position of the register marks 9 relative to the angle of rotation of the engraved cylinder 11 is determined using a reader unit 14. Using an adjustable system of deflection rollers 15, the advance run of the film web ahead of the engraved cylinder 11 is then adjusted in such a manner that the adhesive frames 6 are applied to the carrier film 2 at a position that has been predetermined with regard to the register marks 9.

Subsequently, a web of textile material 3, which has a surface structure that is suitable for being connected with hook and loop hooks, is applied to the side of the carrier film 2 to which adhesive has been applied. The two-layer web 16 formed in this manner passes through the roller gap of a roller pair 17, in which the carrier film is pressed together with the textile material. Finally, laminate material elements are cut out of the laminate material. The register marks 9 imprinted on the carrier film can be used for cutting accurately in accordance with the register.

Cutting does not have to take place directly after the lamination process, but rather can also take place only immediately before the further processing, e.g. within the course of diaper production. In this case, it is practical if the laminate material is processed as rolled goods. The adhesive areas referred to as adhesive frames 6 result in less dust formation during cutting of the laminate material. Since the cut takes place in the zones that are glued over their entire area, no loose fiber residues and filament residues are formed; these could contaminate the system as dust.

Accordingly, while only a few embodiments of the present invention have been shown and described, it is obvious that many changes and modifications may be made thereunto without departing from the spirit and scope of the invention.

What is claimed is:

1. Laminate material element for a hook and loop closure, particularly a diaper closure, comprising:
   a carrier film and a textile material laminated onto the carrier film;
   said carrier film being imprinted;
   said textile material comprising a warp-knitted material, which is translucent so that the print of the carrier film remains visible and which has a basic interlaid scrim of filament yarns and loops connected with the basic interlaid scrim by means of knitting technology which are suitable for forming a connection with hooks of a hook and loop closure;
   The carrier film and the textile material being glued to one another, by means of an adhesive, wherein the adhesive is applied over the entire area between the carrier film and the textile material in an edge region that extends along edges of the laminate material element and said edge region forms an adhesive frame; and
   wherein the adhesive is arranged in an adhesive pattern in the region within the frame consisting of adhesive covered areas and regions that are free of adhesive.

2. Laminate material element according to claim 1, wherein the proportion of the adhesive-covered area is 20% to 80% with reference to the region surrounded by the adhesive frame (6).

3. Laminate material element according to claim 1, wherein the carrier film (2) and the region material (3) are glued together in a dot pattern in the region surrounded by the adhesive frame.

4. Laminate material element according to claim 1, wherein the adhesive forms a pattern of parallel or intersecting stripes within the adhesive frame (6).

5. Laminate material element according to claim 1, wherein the adhesive forms a pattern having a cell-shaped structure within the adhesive frame (6).

6. Laminate material element according to claim 1, wherein the edge region that is bonded over the entire surface has a width of 5 mm to 30 mm.

7. Laminate material element according to claim 1, wherein the region within the frame-shaped edge region has a length between 20 mm and 100 mm, and a width between 50 mm and 500 mm.

8. Laminate material element according to claim 1, wherein the textile material (3) has a weight per unit area of from 5 g/m² to 50 g/m².

9. Laminate material element according claim 1, wherein the carrier film (2) is also embossed.

* * * * *